United States Patent [19]

Wu et al.

[11] 4,280,924

[45] * Jul. 28, 1981

[54] REGENERATING PEROSMATE CATALYST

[75] Inventors: Ching-Yong Wu, O'Hara Township, Allegheny County; Thaddeus P. Kobylinski, Gibsonia, both of Pa.

[73] Assignee: Gulf Research & Development Company, Pittsburgh, Pa.

[*] Notice: The portion of the term of this patent subsequent to Aug. 12, 1997, has been disclaimed.

[21] Appl. No.: 107,867

[22] Filed: Dec. 28, 1979

Related U.S. Application Data

[63] Continuation-in-part of Ser. No. 972,929, Dec. 26, 1978, Pat. No. 4,217,291.

[51] Int. Cl.$^3$ ............... B01J 31/40; B01J 23/96; C07C 29/03; C07C 27/16
[52] U.S. Cl. .................. 252/416; 252/414; 568/860; 260/429 R
[58] Field of Search .................. 252/412, 414, 416; 568/860; 423/22, 593; 260/429 R

[56] References Cited

U.S. PATENT DOCUMENTS

| | | | |
|---|---|---|---|
| 3,317,592 | 5/1967 | MacLean et al. | 252/412 |
| 4,049,724 | 9/1977 | Sheng et al. | 568/860 |
| 4,217,291 | 8/1980 | Wu et al. | 252/414 |

*Primary Examiner*—P. E. Konopka
*Attorney, Agent, or Firm*—Deane E. Keith; Forrest D. Stine; Donald L. Rose

[57] ABSTRACT

A catalyst residue containing osmium catalyst having a substantial component with a valency state less than +5 is regenerated to a valency state greater than +5 by contacting the residue with an organic hydroperoxide at a pH greater than 7 and the regenerated catalyst residue is recycled to a hydroxylation reactor containing ethylene or propylene, a polar organic solvent, an aqueous solution of cesium, rubidium, potassium or tetraalkylammonium hydroxide and an organic hydroperoxide.

11 Claims, No Drawings

REGENERATING PEROSMATE CATALYST

This application is a continuation-in-part of our application Ser. No. 972,929, filed Dec. 26, 1978, now U.S. Pat. No. 4,217,291.

SUMMARY OF THE INVENTION

This invention relates to a cyclic procedure in which a perosmate catalyst is regenerated from an osmium catalyst residue by treatment with an organic hydroperoxide and the regenerated perosmate catalyst is fed together with an organic hydroperoxide and ethylene or propylene to a hydroxylation reactor containing an aqueous solution of cesium, rubidium, potassium or a tetra(lower)alkylammonium hydroxide.

DESCRIPTION OF THE INVENTION

When olefins such as ethylene and propylene are hydroxylated using a relatively stable organic hydroperoxide and an osmium (VIII) catalyst, the osmium (VIII) is reduced to catalytically inactive osmium (VI) which is then instantly oxidized back to the osmium (VIII) by the hydroperoxide. The mechanism of this reaction appears to involve the osmium compound as the carrier of the oxygen from the hydroperoxide to the olefin. Since the olefin is used in substantial stoichiometric excess over the hydroperoxide, the hydroperoxide is eventually exhausted and the osmium (VIII) is completely reduced to osmium (VI). If the osmium catalyst residue is recovered and recycled in the process, the catalytically inactive osmium (VI) is reoxidized in situ in the reactor to the catalytically active osmium (VIII) by the fresh charge of the hydroperoxide oxidizer. However, we have discovered that a minor amount of the osmium (VI) is further reduced to osmium (III) and/or osmium (IV) in the reactor after the hydroperoxide has been exhausted and have further discovered that this osmium (III) or osmium (IV) is not regenerated in situ by the fresh charge of hydroperoxide following recycle. As a result, the catalytically inactive osmium (III) or osmium (IV) builds up upon repeated recycle until the osmium loses its usefulness as a catalyst.

We have discovered that the cyclic process can be operated over repeated cycles without significant loss of catalyst activity, if the catalyst residue that is recovered from each hydroxylation cycle is subjected to a separate regeneration procedure. In this regeneration procedure we have discovered that the valence states of osmium in the catalyst residue which are lower than +5 can be raised to a valence state higher than +5, if the osmium catalyst residue is contacted with a stable secondary or tertiary organic hydroperoxide at subambient temperatures, that is, temperatures less than 30° C. in the absence of any other compound which is reactive with the hydroperoxide. Under these conditions the osmium is oxidized to a valence higher than +5, that is substantially completely to Os(VIII). If ambient or superambient temperatures are used, that is temperatures of about 30° C. and higher, the osmium catalyzes the decomposition of the hydroperoxide causing substantial loss of hydroperoxide with only minimum oxidation of the osmium to a higher valence state.

The hydroxylation reaction is carried out using a secondary or tertiary organic hydroperoxide, water, a strong alkali, an osmium (VIII) catalyst and a suitable solvent. Any secondary or tertiary organic hydroperoxide can be used which is stable at the hydroxylation conditions. Included in this group of useful hydroperoxides are ethylbenzene hydroperoxide, cumene hydroperoxide, tert-butyl hydroperoxide, tert-pentyl hydroperoxide, 1-phenylcyclohexyl hydroperoxide, and the like. The amount of hydroperoxide used in the reaction is not critical but will generally be from about one to about 20 weight percent of the total reaction mixture, preferably from about five to about 20 percent of the reaction mixture.

The strong alkali which we prefer for the hydroxylation reactor is cesium hydroxide, rubidium hydroxide, potassium hydroxide or tetra(lower)alkylammonium hydroxide. Sodium hydroxide is unsatisfactory. The hydroxide can be conveniently added as a water solution. No more water is needed in the reaction mixture than that amount used to solubilize the base. This base is used in an amount between about 0.1 and a maximum of about five weight percent of the reaction mixture for the organic base and a maximum of about ten weight percent for the inorganic base, but we prefer that at least about 0.2 weight percent of the base be used up to a preferred maximum of about two weight percent of the organic base and a maximum of about five weight percent of the inorganic base. When the organic base is used, the reaction mixture is a single-phase, homogeneous mixture. However, when the inorganic base is used, the reaction mixture is a two-phase, heterogeneous mixture. The pH of the reaction mixture, including both phases in the heterogeneous mixture, will be about 14 as a result of the presence of the strong base.

The osmium catalyst is used in catalytic quantities. We find that about 0.01 to about ten millimols of the osmium per 100 milliliter of the reaction mixture is suitable, however we prefer to carry out the hydroxylation reaction in the presence of between about 0.03 to about one millimol of the osmium catalyst per 100 ml of the reaction mixture. The catalyst that we use is cesium, rubidium, potassium or tetra(lower)alkylammonium perosmate. However, we can also use the osmate of these cations in which the osmium is present as osmium (VI) because the osmate is converted in situ to the osmium (VIII) perosmate by the hydroperoxide in the hydroxylation reactor. We can also add osmium tetroxide to the hydroxylation reactor because this readily converts to the perosmate by the base which is present in the reactor. However, once the reaction has been initiated, the regenerated perosmate will be fed to the reactor with only slight amounts of make-up osmium catalyst being necessary.

We prefer to carry out the hydroxylation reaction using an organic polar solvent. The organic polar solvent can be an aliphatic or aromatic alcohol having from one to about ten carbon atoms, an aliphatic or aromatic ketone having from three to about ten carbon atoms, an aliphatic or alicyclic ether having from two to about ten carbon atoms, a glycol having from two to about ten carbon atoms, a N,N-dialkyl amide having from three to about ten carbon atoms, an aliphatic or aromatic sulfoxide having from two to about fourteen carbon atoms, an aliphatic or aromatic sulfone having from two to about fourteen carbon atoms, and the like. Examples of suitable polar solvents include methanol, ethanol, propanol, butanol, hexanol, decanol, benzyl alcohol, acetone, methylethyl ketone, methylbutyl ketone, acetophenone, ethylene glycol, propylene glycol, diethylene glycol, tetraethylene glycol, dimethyl formamide, diethyl formamide, dimethyl acetamide, dimethyl sulfoxide, diethyl sulfoxide, di-n-butyl sulfoxide, diphenyl sulfoxide, dibenzyl sulfoxide, dimethyl sulfone, diethyl sulfone, tetramethylene sulfone, diphenyl sulfone, acetonitrile, pyridine, dioxane, tetrahydrofuran, tetrahydropyran, dioxolane, and the like. The amount of polar solvent can be between about 30 and about 98 weight percent of the reaction mixture, but will preferably comprise between about 50 and 80 percent of the reaction mixture. The preferred organic polar solvents are those which resist oxidation in the reaction system.

Since an aromatic hydroperoxide such as ethylbenzene hydroperoxide is generally formed as a dilute solution of the hydroperoxide in the hydrocarbon precursor as the solvent, the use of such hydroperoxide will include a significant amount of the hydrocarbon precursor as solvent. As a result, the reaction mixture can contain as much as 50 weight percent of the hydrocarbon precursor solvent or other suitable hydroperoxide solvent, but at preferred conditions of operation it will contain no more than about 30 weight percent of a hydrocarbon solvent. In contrast, an aliphatic hydroperoxide such as tert-butyl hydroperoxide is generally used as a solution with tert-butyl alcohol as the solvent.

Since ethylene and propylene are gases, they are incorporated into the reaction system by pressuring the reactor with the olefin. The pressure is not critical, rather it determines the amount of the olefin that is present in the reaction liquid and therefore affects the rate of reaction. We find that a pressure between about 25 and about 1,500 psig, is useful for ethylene, and a pressure of between about 5 and about 150 psig. is useful for propylene. However, we prefer to operate within a pressure range of between about 50 and about 150 psig. for ethylene and a pressure between about 10 and about 50 psig. for propylene as providing a suitable reaction rate without requiring high pressure equipment. The reaction is preferably carried out with a stoichiometric excess of the olefin to substantially completely react all of the hydroperoxide in the reaction mixture, and more preferably at least about a 25 percent stoichiometric excess of the olefin.

The hydroxylation reaction is carried out at a moderate temperature. At higher temperatures the reaction rate increases substantially but this occurs at a significant reduction in selectivity to the diol. At very low temperatures the selectivity to diol is excellent but the reaction rate is slow. Within those constraints we find that a moderate reaction temperature is desirable including the range of about $-10°$ C. to about $50°$ C., but we prefer to operate within the range of about $0°$ C. to about $25°$ C.

This hydroxylation reaction can be carried out as a batch reaction, or as a semi-continuous batch reaction. In the batch reaction all the necessary components are placed in a reaction vessel and the reaction is allowed to proceed for about one to about 24 hours for substantially complete reaction of the hydroperoxide. The reaction can be carried out in a semi-continuous manner by metering the reaction components into an agitated tank reactor, or into the first of a series of tank reactors, pressured with the olefin and removing the reaction product mixture at an appropriate rate to maintain the reactor liquid level.

The reaction product, after removal of unreacted gaseous olefin, includes the diol, the organic decomposition residue from the hydroperoxide, the hydrocarbon solvent, if used, the polar solvent, the hydroxide, the osmium catalyst residue and water. Since the reaction is generally carried out under conditions, including a stoichiometric excess of olefin for complete reaction of the hydroperoxide, there is no significant amount of hydroperoxide in the reaction product. If unreacted hydroperoxide shows up in the reaction product, it is removed by the use of a suitable reducing agent in an extra processing step as a safety precaution to avoid possible hazards resulting from the undesired decomposition of the hydroperoxide during product work-up. Therefore, insuring the substantial absence of hydroperoxide in the reaction product represents a safety precaution and avoids substantial processing costs.

The volatile components are distilled out of the reaction product into various fractions. The osmium catalyst residue together with base and some associated water remain in the still. Since the osmium in the catalyst residue will be converted to volatile osmium tetroxide in an acid environment, the catalyst residue must be maintained at a pH greater than 7, preferably a pH of at least about 10. Since organic acid by-products frequently are produced in the preparation of organic hydroperoxides, these acids, if added with the hydroperoxide, will neutralize the base. The desired pH can be maintained by adding more base, if required, preferably the same base that is used in the succeeding hydroxylation cycle. If it should be necessary to separate out and recover the osmium from the residue, the residue can be acidified with nitric acid to evaporate the resulting osmium tetroxide which can then be condensed.

Since many organic compounds will reduce osmium (VIII) to a lower valency state, it is essential that any organic compound which will reduce osmium (VIII) be excluded from the reaction zone in which the osmium catalyst is regenerated. If this is not done the regeneration is ineffective or only partially effective. It is for this reason that the organic components in the hydroxylation reaction product are substantially completely removed from the osmium catalyst residue before it is regenerated.

Any organic secondary and tertiary hydroperoxide, which is substantially stable, at the subambient temperature used in the regeneration can be used for the regeneration reaction. This includes hydroperoxides such as ethylbenzene hydroperoxide, cumene hydroperoxide, t.butyl hydroperoxide, t.pentyl hydroperoxide, 1-phenyl cyclohexyl hydroperoxide, and the like. We have attempted to regenerate a deactivated osmium catalyst with hydrogen peroxide at a subambient temperature and discovered that the hydrogen peroxide was completely decomposed without catalyst regeneration.

Since the hydroperoxide is generally prepared by the partial oxidation of its hydrocarbon precursor, the hydroperoxide can be used in the regeneration reaction in solution with its percursor compound, such as ethylbenzene hydroperoxide in ethylbenzene. Or the hydroperoxide can be used in solution in a solvent which is not oxidizable by the osmium (VIII) compound, such as t.butyl hydroperoxide in t.butanol or water. Sufficient hydroperoxide is preferably added to regenerate all of the osmium in the residue to osmium (VIII) and most preferably a moderate excess is added to insure complete regeneration of the osmium.

The present process for the oxidation of osmium in ionic compounds and for the regeneration of ionic osmium catalysts is carried out at a temperature below about $30°$ C., since osmium catalyzes the significant undesired decomposition of hydroperoxides at about $30°$ C. and higher. Therefore, the present process is carried out at a temperature less than 30° C., preferably a temperature between about −10° C. and about 25° C., and most preferably a temperature between about 0° C. and about 20° C.

The osmium catalyst that has been regenerated in this manner can be reused in repeated hydroxylation cycles without a measurable loss in selectivity. However, when the catalyst regeneration procedure is omitted the catalyst quickly becomes inactive. For example, when ethylene was hydroxylated using tetraethylammonium perosmate and ethylbenzene hydroperoxide in aqueous tetraethylamonium hydroxide, the yield of diol was 67.3 percent. After the fourth recycle of this catalyst without regeneration, the yield had decreased to two percent.

DESCRIPTION OF PREFERRED EMBODIMENTS

Example 1

A charge of 100 ml. of t.butanol and 7.5 ml. of ten percent aqueous tetraethylammonium hydroxide was placed in a 300 ml. thick-walled glass reactor equipped with a thermocouple and a stirring magnet. The solution was cooled to 0° C. in an ice-salt bath. After adding 59 g. of twenty percent ethylbenzene hydroperoxide in ethylbenzene (80 mmols) to the chilled solution, the reactor was sealed. Ethylene was introduced into the reactor to a pressure of about 120 psi. Then 5 ml. of 0.5 percent osmium tetroxide (0.1 mmol) in t.butanol was pressured into the reactor in a stream of ethylene. The ethylene pressure was adjusted to 150 psi. and the reaction was allowed to proceed for six hours at 0° C. and at about 150 psi (1.03 MPa). The reactor was then permitted to stand overnight at room temperature. The reaction product was analyzed by gas-liquid chromatography and showed 3.16 g. of ethylene glycol which was a 63.6 percent yield of ethylene glycol based on the ethylbenzene hydroperoxide charged.

Example 2

The reaction product from Example 1 was evaporated at 90° C. and a pressure of five mm. to remove most of the organic components. There was obtained less than five ml. of a residue of the osmium catalyst. It was cooled to 0° C. and stirred with 10 ml of 20 percent ethylbenzene hydroperoxide for 4 hours. The mixture was warmed to room temperature and left standing overnight. Next morning a small sample of the mixture was titrated iodometrically to make sure there was no unreacted ethylbenzene hydroperoxide left. The color of the regenerated catalyst mixture had changed from dark brown to brownish yellow.

Example 3

The regenerated catalyst mixture from Example 2 was diluted to 100 ml. with t.butanol and mixed with 7.5 ml. 10 percent aqueous solution of tetraethylammonium hydroxide. The solution was placed in a glass reactor and cooled to 0° C. The reactor was sealed and pressured to 120 psi. with ethylene. Then 59 ml. of 20 percent ethylbenzene hydroperoxide (80 mmols) was introduced from a charge tube connected to the reactor by means of extra ethylene pressure. The ethylene pressure was adjusted to 150 psi. and maintained at this pressure. The reaction was run for 6 hours at 0° C. and left overnight at room temperature. The reaction product was analyzed by gas-liquid chromatography and found to contain 3.24 g. of ethylene glycol, a yield of 65.3 percent.

Example 4

The catalyst residue from Example 3 was recovered and regenerated as described in Example 2 and reused as described. The reaction product was found to contain 3.02 g. of ethylene glycol by gas-liquid chromatography which was a yield of 60.8 percent.

Example 5

Recovery, regeneration and reuse of the catalyst residue from Example 4 in the same manner as described resulted in the production of 3.12 g. of ethylene glycol which was a yield of 62.9 percent.

Example 6

When this recovery, regeneration and reuse cycle was repeated on the catalyst residue from Example 5, 3.10 g. of ethylene glycol were found in the product, a yield of 62.5 percent.

Example 7

A further recovery, regeneration and recycle stage was carried out on the catalyst residue obtained from Example 6 and this product analyzed 3.13 g. of ethylene glycol, which was a 63.0 percent yield.

Example 8

The final recovery, regeneration and reuse procedure was carried out on the catalyst residue resulting from Example 7. This final product showed 2.79 g of ethylene glycol by gas-liquid chromatographic analysis, which was 56.1 percent yield.

It is to be understood that the above disclosure is by way of specific example and that numerous modifications and variations are available to those of ordinary skill in the art without departing from the true spirit and scope of the invention.

We claim:

1. A cyclic process for the regeneration of a perosmate catalyst which comprises the steps
   (a) contacting ethylene or propylene at an elevated pressure in a hydroxylation reactor with a reaction mixture comprising a secondary or tertiary organic hydroperoxide in the presence of a catalytic amount of cesium perosmate, rubidium perosmate, potassium perosmate or tetra(lower)alkylammonium perosmate, an organic polar solvent and an aqueous solution containing cesium hydroxide, rubidium hydroxide, potassium hydroxide or a tetra(lower)alkylammonium hydroxide at a moderate temperature until said hydroperoxide is substantially exhausted whereby a portion of said osmium is reduced to a valence state less than +5,
   (b) recovering an osmium-containing catalyst residue from the product mixture,
   (c) oxidizing that portion of the osmium in the catalyst residue which is at a valence state less than +5 to a valence state greater than +5 by contacting the osmium catalyst residue with a secondary or tertiary organic hydroperoxide at a temperature less than about 30° C. and at a pH greater than 7, and
   (d) recycling the regenerated perosmate catalyst to the hydroxylation reactor.

2. A cyclic process for the regeneration of a perosmate catalyst in accordance with claim 1 in which said hydroperoxide is ethylbenzene hydroperoxide, cumene hydroperoxide, tert-butyl hydroperoxide, tert-pentyl hydroperoxide or 1-phenyl cyclohexyl hydroperoxide.

3. A cyclic process for the regeneration of a perosmate catalyst in accordance with claim 1 in which said hydroperoxide is ethylbenzene hydroperoxide.

4. A cyclic process for the regeneration of a perosmate catalyst in accordance with claim 1 in which the said osmium catalyst residue is at a pH of at least about 10.

5. A cyclic process for the regeneration of a perosmate catalyst in accordance with claim 1 in which the said osmium catalyst residue is contacted with said hydroperoxide at a temperature between about −10° C. and about 25° C.

6. A cyclic process for the regeneration of a perosmate catalyst in accordance with claim 1 in which said moderate temperature is a temperature between about −10° C. and about 50° C.

7. A cyclic process for the regeneration of a perosmate catalyst in accordance with claim 1 in which there is between about 0.01 and about ten mmols of osmium per 100 ml of reaction mixture.

8. A cyclic process for the regeneration of a perosmate catalyst in accordance with claim 1 in which there is between about 0.1 and about ten weight percent of said hydroperoxide in said reaction mixture.

9. A cyclic process for the regeneration of a perosmate catalyst in accordance with claim 1 in which the olefin is ethylene and the pressure is between about 50 and about 150 psig.

10. A cyclic process for the regeneration of a perosmate catalyst in accordance with claim 1 in which the reaction mixture contains between about 30 and about 80 weight percent of said polar solvent.

11. A cyclic process for the regeneration of a perosmate catalyst in accordance with claim 2 in which the reaction mixture contains between about one and about 20 weight percent of said hydroperoxide.

* * * * *